US00PP11966P2

(12) United States Plant Patent
van Veen

(10) Patent No.: US PP11,966 P2
(45) Date of Patent: Jun. 26, 2001

(54) ASTILBE PLANT NAMED 'LOLLYPOP'

(75) Inventor: Wim van Veen, Noorden (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/473,566

(22) Filed: Dec. 29, 1999

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Astilbe plant named 'Lollypop', characterized by its upright and compact plant habit; dark green leaves; dark purple-colored stems and petioles; freely and uniformly flowering; and attractive pink-colored flowers.

2 Drawing Sheets

BACKGROUND OF THE INVENTION

The present invention relates to a new and distinct cultivar of Astilbe plant, botanically known as Astilbe hybrid, and hereinafter referred to by the cultivar name 'Lollypop'.

The new cultivar is a product of a planned breeding program conducted by the Inventor in Noorden, The Netherlands. The objective of the breeding program was to develop new Astilbe cultivars with dark stems and attractive flower colors.

The new cultivar originated from a cross made by the Inventor in 1992 of the Astilbe×Arendsii cultivar 'Grete Pungel', not patented, as the male or pollen parent, with the *Astilbe japonica* cultivar 'Europa', not patented, as the female or seed parent.

The cultivar 'Lollypop' was discovered and selected by the Inventor as a flowering plant within the progeny of the stated cross in a controlled environment in Noorden, The Netherlands.

Asexual propagation of the new cultivar by divisions harvested at Noorden, The Netherlands, has shown that the unique features of this new Astilbe are stable and reproduced true to type in successive generations.

SUMMARY OF THE INVENTION

Plants of the cultivar 'Lollypop' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Lollypop'. These characteristics in combination distinguish 'Lollypop' as a new and distinct cultivar:

1. Upright and compact plant habit.
2. Dark green leaves.
3. Dark purple-colored stems and petioles.
4. Freely and uniformly flowering.
5. Attractive pink-colored flowers.

Plants of the new Astilbe differ from plants of the male parent, the cultivar 'Grete Pungel', in inflorescence shape. In addition, plants of the new Astilbe are narrower and have fewer flowers than plants of the cultivar 'Grete Pungel'.

Plants of the new Astilbe differ from plants of the female parent, the cultivar 'Europa', in flower and leaf color, in addition, plants of the new Astilbe are more compact and have smaller leaves than plants of the cultivar 'Europa'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Astilbe.

The photograph on the first sheet comprises a side perspective view of a typical plant of the new Astilbe.

The photograph at the top of the second sheet comprises a close-up view of typical inflorescences of the new Astilbe.

The photograph at the bottom of the second sheet comprises a close-up view of a typical leaf of the new Astilbe.

DETAILED BOTANICAL DESCRIPTION

In the following description, color references are made to The Royal Horticultural Society Colour Chart exept where general terms of ordinary dictionary significance are used. Plants used for the description were about one year-old and grown in 17-cm containers under outdoor production conditions which closely approximate commercial production conditions during the spring and summer in Noorden, The Netherlands.

Botanical classification: Astilbe hybrid cultivar 'Lollypop'.
Parentage:
- *Female parent.*—*Astilbe japonica* cultivar 'Europa', not patented.
- *Male parent.*—Astilbe×Arendsii cultivar 'Grete Pungel', not patented.

Propagation:
- *Type.*—By root divisions.
- *Time to rooting.*—About 3 months at temperatures about 18° C.
- *Root description.*—Fine.

Plant description:

*Crop time.*—From divisions, about 40 weeks are required to produce fully-grown flowering plants in 17-cm containers.

*Form.*—Upright, compact; inverted triangle.

*Branching habit.*—Flowering stems and leaves arise from the roots.

*Plant height.*—About 35 cm.

*Area of spread.*—About 30 cm.

*Vigor.*—Moderate.

*Stems.*—Length: About 35 cm. Internode length: About 6 cm. Texture: Very sparsely covered with very short (less than 0.5 mm) dark purple, 187A, hairs. Color: 187A.

*Foliage description.*—Arrangement: Bi-ternately compound; alternate. Quantity of leaflets per leaf: Typically about 23. Leaf length, including petiole: Up to about 24 cm. Leaf width: About 18 cm. Leaflet length: About 5 cm. Leaflet width: About 1.7 cm. Leaflet shape: Elliptic to narrowly ovate. Leaflet apex: Acuminate to acute. Leaflet base: Acuminate. Leaflet margin: Doubly serrate. Leaflet texture: Lustrous; glabrous. Leaflet color: Young and mature foliage, upper surface: 136A. Young and mature foliage, lower surface: 147A to 147B. Venation, upper surface: 138A. Venation, lower surface: 187D. Petiole: Length: About 8 cm. Diameter: About 2 mm. Texture: Smooth. Color: 187A.

Flower description:

*Flower type and habit.*—Numerous small single flowers arranged in branched panicles. Very freely flowering with about 250 to 300 flowers and flower buds per flowering stems. Flowers sessile.

*Natural flowering season.*—Continuously flowering typically during the early summer.

*Flower longevity.*—Flowers last a few weeks on the plant and more than one week as a cut flower. Flowers persistent.

*Fragrance.*—Faint, not unpleasant.

*Flower buds.*—Length: About 2 mm. Diameter: About 1.5 mm. Shape: Ovate. Rate of opening: About two to three weeks from visible bud to fully opened flower. Color: 68C.

*Flower size.*—Length (height): About 4 mm. Diameter: About 2 mm.

*Petals.*—Arrangement: Five. Shape: Linear to oblanceolate; ligulate. Apex: Obtuse. Margin: Entire. Length: About 2 mm. Width: About 1 mm. Texture: Smooth. Color: When opening, upper and lower surfaces: 68B. Fully opened flower, upper and lower surfaces: 68B; flower color fading to slightly paler than 68B.

*Calyx.*—Length: About 3 mm. Width: About 2 mm. Number of sepals: About five. Sepal shape: Ovate. Sepal apex: Obtuse. Sepal margin: Entire. Sepal color (Both surfaces): Close to 142D.

*Reproductive organs.*—Stamens: Stamen number: About ten. Anther attachment: Basifixed. Anther length: Less than 0.5 mm. Anther color: Pale creamy pink. Pollen amount: Scarce. Pollen color: Creamy white. Pistils: Pistil number: Two. Pistil length: About 2 mm. Stigma shape: Club-shaped. Stigma color: Close to 68B. Style length: About 1.5 mm. Style color: Close to 68C to 68D. Ovary color: Greenish pink.

*Seed.*—Length: Less than 0.5 mm. Diameter: Less than 0.5 mm. Color: Light brown.

Disease resistance: Under commercial conditions, plants of the new Astilbe have not been observed to be resistant to diseases common to Astilbe.

It is claimed:

1. A new and distinct cultivar of Astilbe plant named 'Lollypop', as illustrated and described.

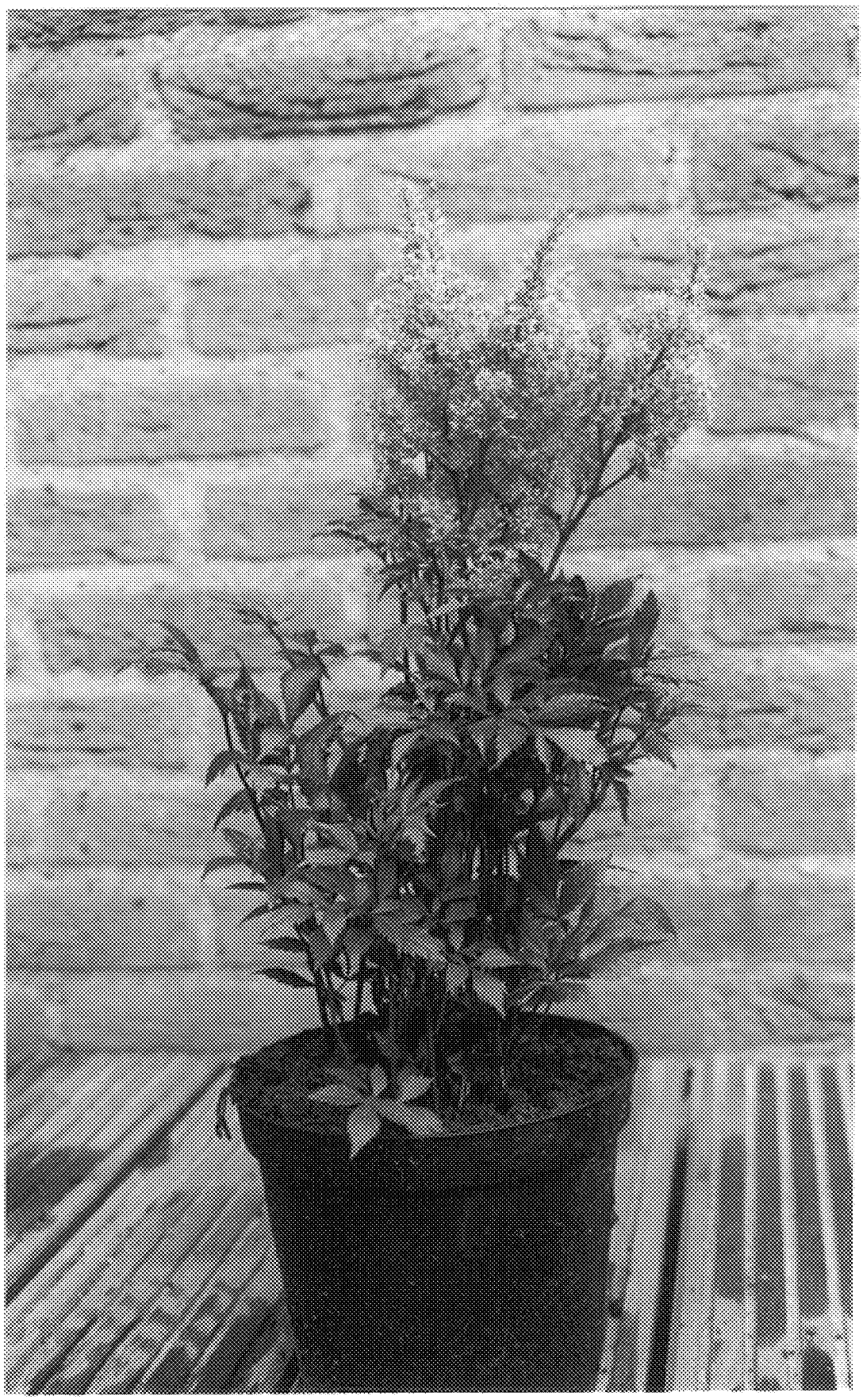

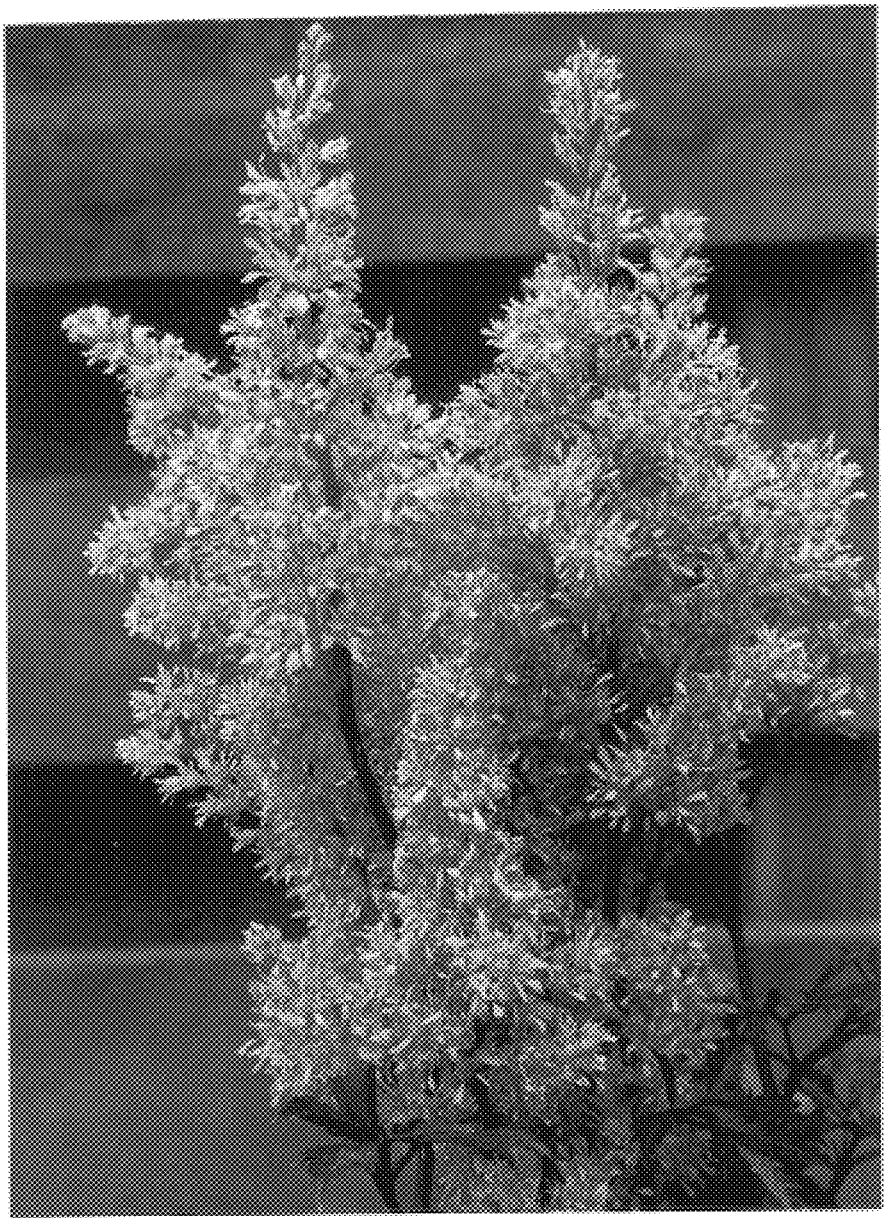
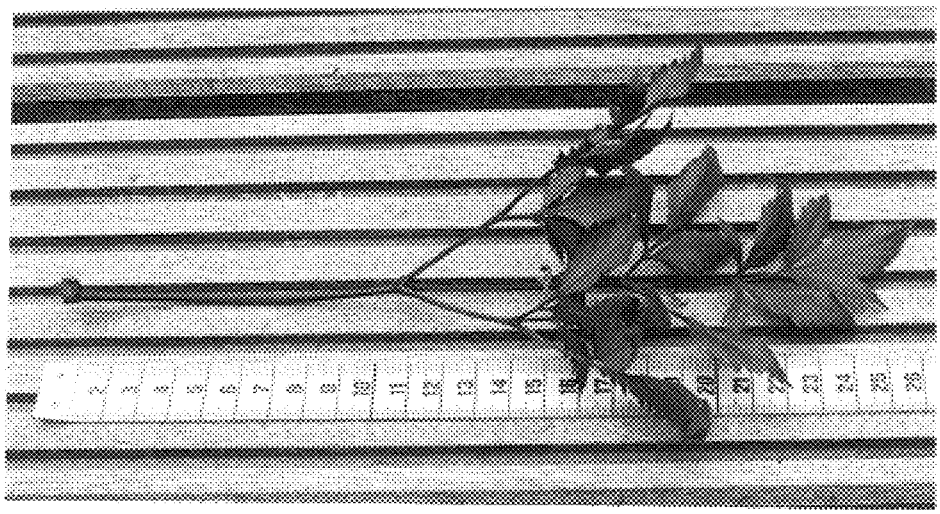

* * * * *